United States Patent
Nagle et al.

(10) Patent No.: US 7,712,373 B2
(45) Date of Patent: May 11, 2010

(54) SENSOR DEVICE FOR REAL-TIME MONITORING OR RELATIVE MOVEMENT USING CAPACITIVE FABRIC SENSORS

(76) Inventors: H. Troy Nagle, 1B Hoath Pl., Durham, NC (US) 27705; Tae-Ho Kang, #114-1202, Narumae Apt., 55 Gajang-dong, Seo-gu, Taejon, 302-726 (KR); Carey Merritt, 3523 Violet Ct., Wilmington, NC (US) 28409; Burcak Karaguzel, Ortahisar Konuttar, Akdeniz Cad. Koru Sok., B2 Blok, Daire: 13, Kat: 7, Beylikdüzü/Istanbul (TR); Behnam Pourdeyhimi, 108 Tropez La., Cary, NC (US) 27511; Edward Grant, 3909 Bluffwind Dr., Raleigh, NC (US) 27603

( * ) Notice: Subject to any disclaimer, the term of this patent is extended or adjusted under 35 U.S.C. 154(b) by 92 days.

(21) Appl. No.: 11/681,329

(22) Filed: Mar. 2, 2007

(65) Prior Publication Data

US 2008/0000304 A1 Jan. 3, 2008

Related U.S. Application Data

(60) Provisional application No. 60/743,404, filed on Mar. 3, 2006.

(51) Int. Cl.
G01B 7/16 (2006.01)
(52) U.S. Cl. .................... 73/780
(58) Field of Classification Search ............ 73/780
See application file for complete search history.

(56) References Cited

U.S. PATENT DOCUMENTS

| | | | |
|---|---|---|---|
| 4,790,968 A | | 12/1988 | Ohkawa et al. |
| 5,137,842 A | * | 8/1992 | Chan et al. ............... 438/254 |
| 5,371,326 A | | 12/1994 | Clearwaters-Dreager et al. |
| 5,371,657 A | | 12/1994 | Wiscombe |
| 6,037,621 A | * | 3/2000 | Wilson .................. 257/296 |
| 6,311,350 B1 | | 11/2001 | Kaiserman et al. |
| 6,826,968 B2 | * | 12/2004 | Manaresi et al. ........ 73/862.046 |
| 7,047,818 B2 | * | 5/2006 | Dallenbach et al. .......... 73/780 |
| 7,299,083 B2 | * | 11/2007 | Drakulic .................. 600/372 |
| 7,353,713 B2 | * | 4/2008 | Harish et al. .............. 73/780 |

FOREIGN PATENT DOCUMENTS

WO WO 2007/056557 A1 5/2007

\* cited by examiner

*Primary Examiner*—Lisa M Caputo
*Assistant Examiner*—Octavia Davis

(57) ABSTRACT

A capacitive sensor device, including electrode materials carried by fabric substrates, is provided for monitoring relative movement of an expanding and/or contracting structure, such as the mammalian chest and/or torso, corresponding to a performance parameter related, for example, to respiratory function. Some embodiments include non-woven fabric substrates comprising compliant portions configured to stretch only in a selected direction and non-compliant portions upon which electrode materials are disposed. In some embodiments, layers of fabric substrates, carrying corresponding first and second electrode materials, are configured to cooperate to form a parallel plate capacitive sensor having a variable capacitance corresponding to a relative motion of the fabric substrates.

33 Claims, 9 Drawing Sheets

SENSOR DEVICE FOR REAL-TIME MONITORING OR RELATIVE MOVEMENT USING CAPACITIVE FABRIC SENSORS

CROSS-REFERENCE TO RELATED APPLICATIONS

This application claims priority from U.S. Provisional Application No. 60/743,404, filed Mar. 3, 2006, which is hereby incorporated by reference herein in its entirety.

FIELD OF THE INVENTION

The various embodiments of the present invention relate generally to the use capacitive fabric sensors for real-time monitoring of structures that expand and/or contract, such as the human torso during respiration.

BACKGROUND OF THE INVENTION

Electronic textiles (e-textiles) is an emerging interdisciplinary field of research that encompasses electronics, materials science, and textiles. E-textiles aim to integrate electronic circuits, sensors, computing elements, and communication into multi-functional textile products and/or apparel. By using textile processes, such as sewing, weaving, and embroidering, sensors may be fabricated upon or within flexible substrates that may be directly integrated into wearable garments. The e-textile approach has significant advantages over conventional sensors fabricated using traditional printed circuit boards in that these e-textiles are less bulky and may be made to move and/or stretch in the manner of the garment into which they are integrated.

Some e-textiles have been developed to detect motion, expansion, and/or contraction that is indicative, for example, of breathing in a wearer of the e-textile garment. In such existing e-textiles, strain gauge sensors are fabricated from polypyrrole (PPy) conductive yarns, or from carbon-filled rubber (CFR) coated conductive yarns. These yarns may be used to construct threads which may be woven or knitted to form a sensor within a textile substrate. While such conventional e-textile sensors exhibit piezoresistive properties when stretched, such sensors also exhibit some undesirable characteristics such as inconsistent loading and unloading properties due to quality control issues in weaving and/or knitting the "sensor" threads into the textile substrates. In summary, it may be difficult to form complex sensor patterns in e-textiles that utilize a knitted and/or woven fabric substrate wherein semi-metallized and/or metal conductive yarns are sewn into such substrates. Furthermore, processes for sewing conductive materials into a knitted and/or woven substrate are time-consuming and error prone, which adds to the complexity and cost of producing e-textile sensors and/or garments utilizing such sensors.

Thus, there exists a need in the art for an e-textile sensor system that addresses the shortcomings of the conventional e-textiles discussed herein. For example, there exists a need for a sensor system that allows for the formation of complex electrode and/or sensor components on or within a fabric substrate such that the sensor system is capable of providing stable, accurate, and precise data over time. In addition, there exists a need in the art for an e-textile sensor system that may be easily manufactured for a relatively low cost.

SUMMARY OF THE INVENTION

The embodiments of the present invention satisfy the needs listed above and provide other advantages as described below.

Embodiments of the present invention may include a sensor device adapted to be operably engaged with an anatomical structure for assessing movement thereof so as to be capable of monitoring an underlying biological function (such as respiratory rate, for example). In some embodiments, the sensor device comprises a first fabric substrate comprising a first compliant portion configured to stretch only in a selected direction, and a first non-compliant portion. The sensor device further comprises a second fabric substrate, disposed substantially parallel to the first fabric substrate. The second fabric substrate may comprise a second compliant portion configured to stretch only in the selected direction and a second non-compliant portion. In some embodiments, at least one of the first fabric substrate and the second fabric substrate may comprise a non-woven fabric that may include, but is not limited to a hydroentangled fiber mat. In some alternate embodiments, at least one of the first fabric substrate and the second fabric substrate may also comprise a woven fabric and/or a combination of woven and non-woven fabrics. Furthermore, in some embodiments, the compliant and non-compliant portions of the fabric substrates may be ultrasonically bonded to form the fabric substrates.

The sensor device also comprises a first electrode material disposed on the first non-compliant portion of the first fabric substrate and a second electrode material disposed on the second non-compliant portion of the second fabric substrate. Thus, according to various sensor device embodiments of the present invention, the first and second electrodes material may be configured to cooperate to form a parallel plate capacitive sensor having a variable capacitance corresponding to a relative motion of the first fabric substrate and the second fabric substrate as the anatomical structure expands and/or contracts. In some embodiments, the variable capacitance may be variable in a substantially linear relationship to the relative motion of the first fabric substrate and the second fabric substrate as the structure expands.

According to various sensor device embodiments, the first and/or second electrode material may comprise conductive materials including, but not limited to: a conductive ink, a conductive foil, and/or combinations of such conductive materials. Furthermore, in sensor device embodiments wherein one or more of the electrode materials comprise a conductive ink, the conductive ink may be screen printed on at least one of the non-compliant portions of the fabric substrates. Alternatively, in sensor device embodiments wherein one or more of the electrode materials comprise a conductive foil, the conductive foil may be operably engaged with at least one of the non-compliant portions using an adhesive coating disposed on the conductive foil and overlapping onto at least a portion of the non-compliant portion of the fabric substrate.

Some additional sensor device embodiments may further comprise a dielectric spacer material disposed between the first electrode material and the second electrode material. In some such embodiments, the dielectric spacer material may comprise an adhesive coating disposed on at least one of the first electrode material and the second electrode material. Furthermore, in order to further insulate the electrode materials (and the parallel plate capacitor formed thereby), some sensor device embodiments may further comprise a first insulating layer disposed between the first electrode material and the first non-compliant portion, and/or a second insulating layer disposed between the second electrode material and the second non-compliant portion.

In order to shield the sensor device from stray electric fields originating outside the sensor device, some embodiments provided herein may further comprise a shield disposed on a side of at least one of the first fabric substrate and the second fabric substrate opposite at least one of the respective first and second electrode materials. In some such embodiments, one or more shields may be in communication with an electrical ground. Furthermore, in other embodiments, the sensor device may further comprise an operational amplifier operably engaged between the shield and the electrode materials.

In some sensor device embodiments, the first electrode material may comprise a first electrode portion and a second electrode portion such that the second electrode material, the first electrode portion, and the second electrode portion may be configured to cooperate to form a differential capacitive sensor having a variable capacitance established between the second electrode material and at least one of the first electrode portion and the second electrode portion. According to such embodiments, the variable capacitance may correspond to the relative motion of the first fabric substrate and the second fabric substrate as the structure expands and/or contracts. Furthermore, in some such embodiments, the first and second electrode portions may be disposed in a substantially interlocking configuration to form a comb electrode.

Some sensor device embodiments may further comprise a transducer circuit in communication with the parallel plate capacitive sensor, the transducer circuit configured for converting the variable capacitance into a corresponding variable voltage indicative of the expansion and/or contraction of the structure. According to such embodiments, the transducer circuit may comprise an RLC oscillator or other detecting circuit configured for converting the variable capacitance into a corresponding frequency shift.

In some embodiments, the first fabric substrate and the second fabric substrate may be formed into layers of a wearable article that may include, but is not limited to: a belt extending substantially about the structure; a shirt; a bandage comprising at least one adhesive material disposed thereon for operably engaging the bandage with the structure; and combinations of such articles. Furthermore, in some such embodiments, the structure may include a patient's torso, and a transducer circuit in communication with the sensor device may be configured for converting a variable voltage generated by the sensor device into an indication of respiratory function corresponding to the expansion and/or contraction of the torso.

Various embodiments of the present invention may also provide methods for measuring a respiratory function. Some such method embodiments comprise steps for engaging a pair of electrodes with an overlapping pair of fabric substrates to form a sensor device comprising a parallel plate capacitor. According to such embodiments, each of the fabric substrates may comprise a compliant portion configured for stretching only in a selected direction. The method further comprises wrapping the sensor device substantially about an anatomical structure (such as a patient's chest, for example). The method further comprises steps for: sensing a change in capacitance in the parallel plate capacitor corresponding to stretching of the compliant portions due at least in part to an expansion and/or contraction of the anatomical structure; and converting the sensed change in capacitance to a signal indicative of the respiratory function, using a processing element in communication with the sensor device.

Thus the various embodiments of the present invention provide many advantages that may include, but are not limited to: providing a sensor system that may be integrated into a wearable garment and/or made conformal to an anatomical structure for measuring movement thereof; providing a textile-based sensor that is capable of measuring changes of length in one dimension; providing a wearable and/or conformal textile-based sensor that may be capable of accurately and precisely measuring respiratory function in a wearer of the sensor.

These advantages, and others that will be evident to those skilled in the art, are provided in the sensor system of the present invention.

BRIEF DESCRIPTION OF THE DRAWINGS

Figure 1:
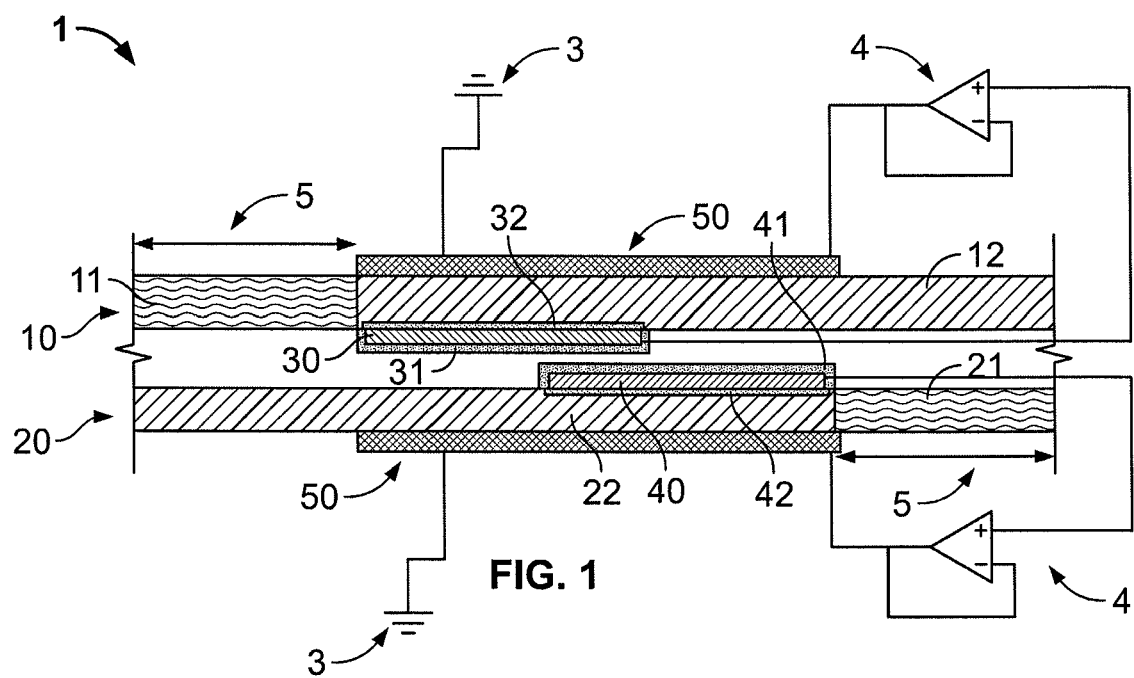
Figure 2A:
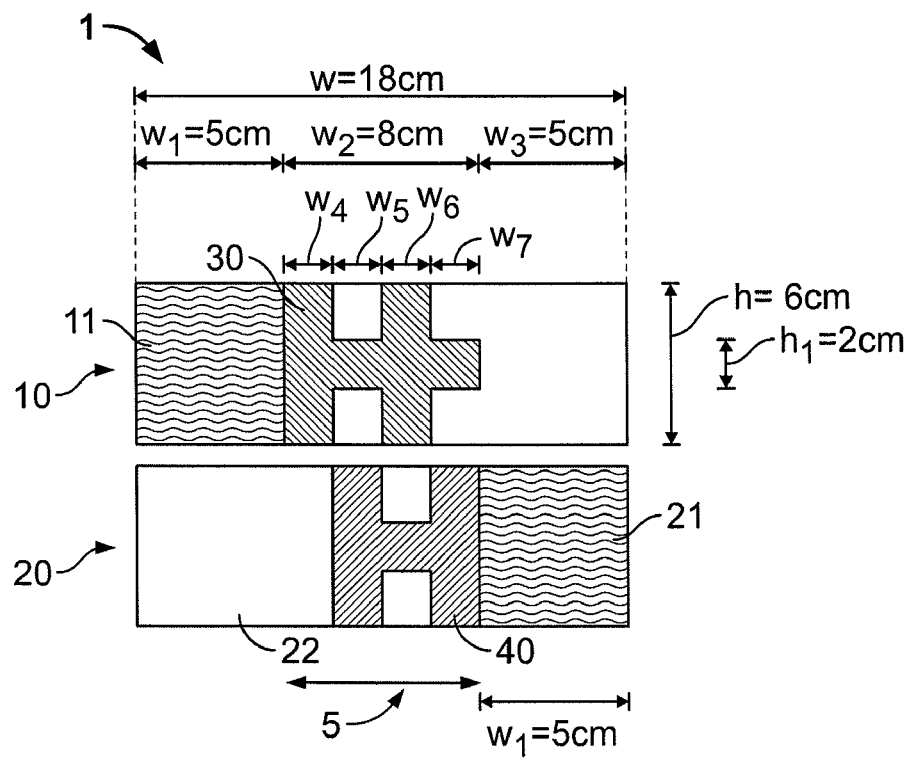
Figure 2B:
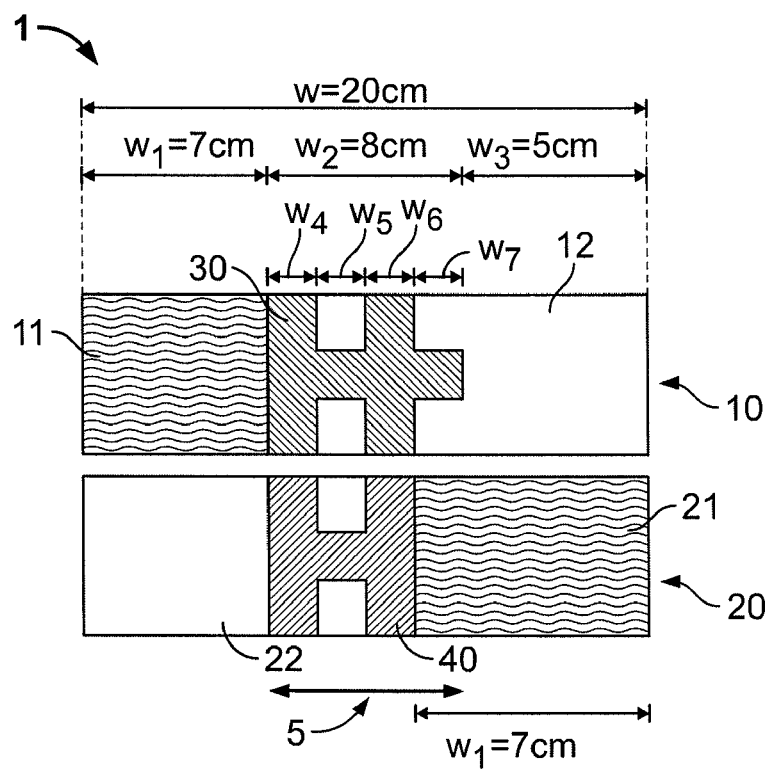
Figure 3A:
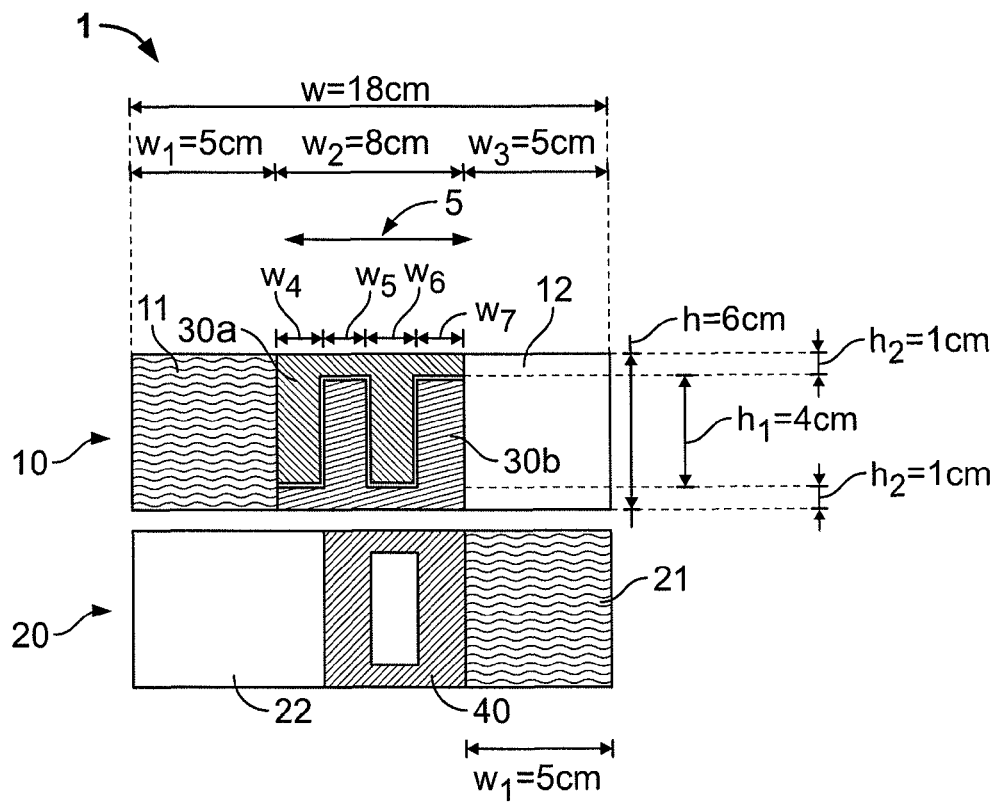
Figure 3B:
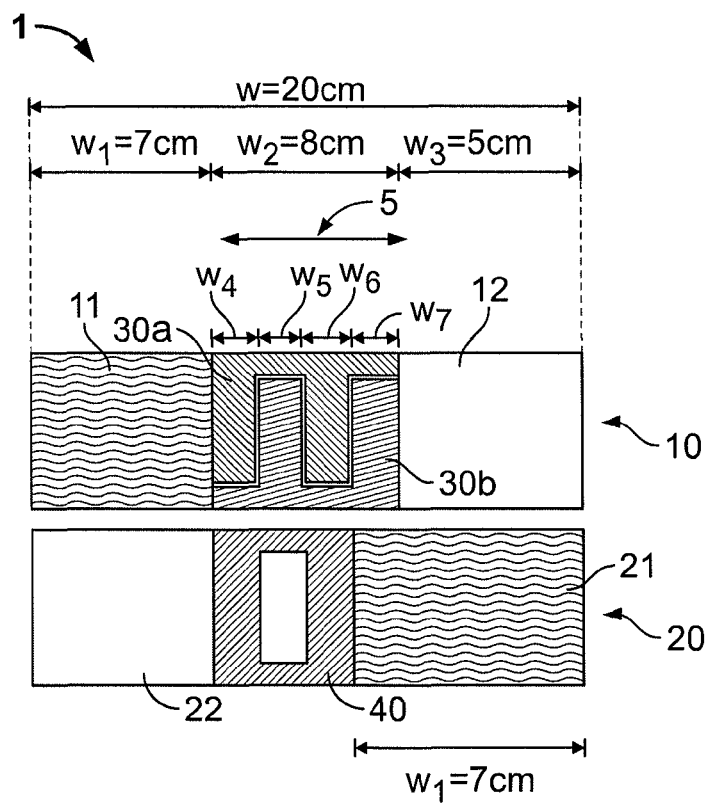
Figure 4:
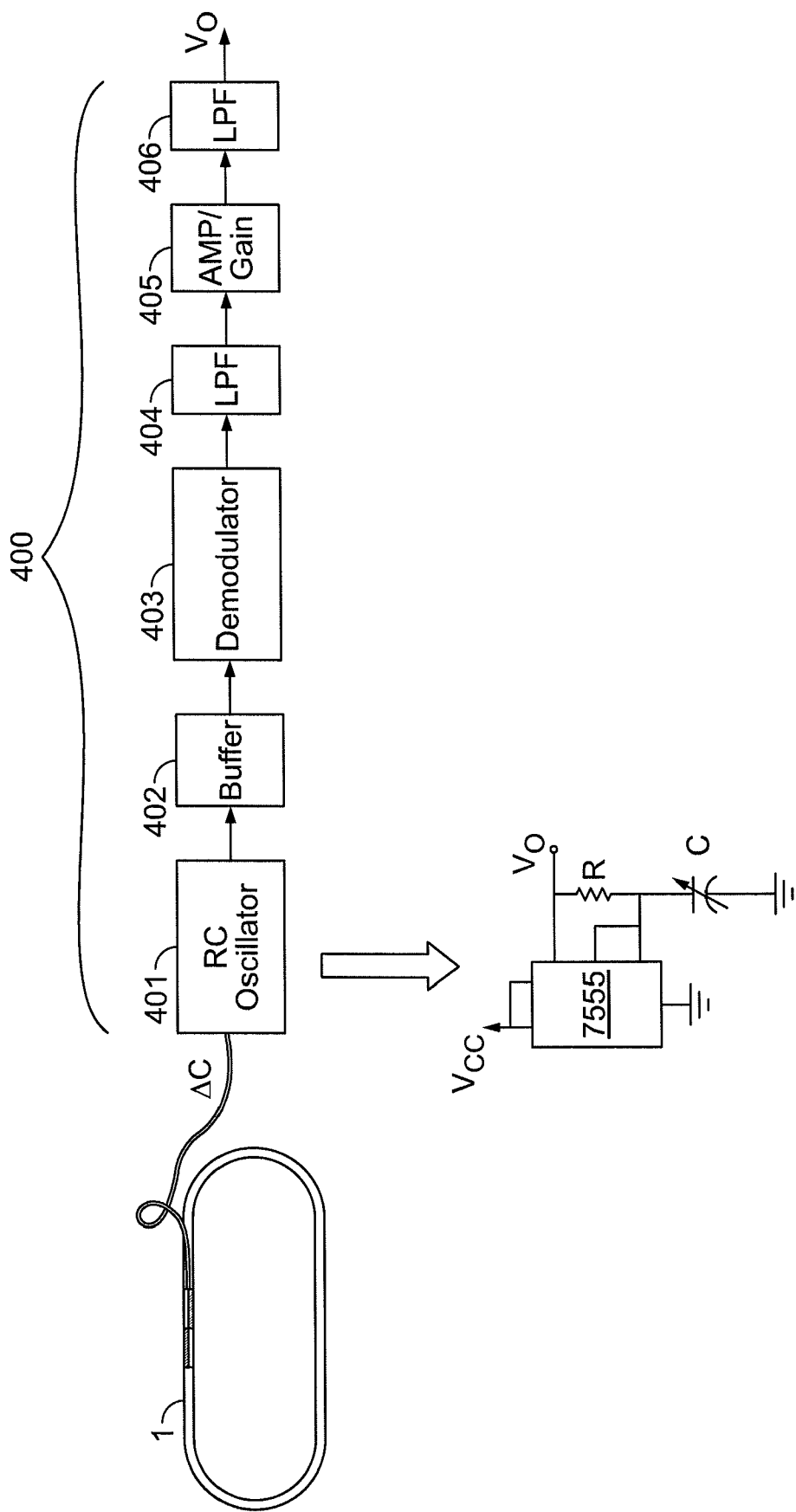
Figure 5:
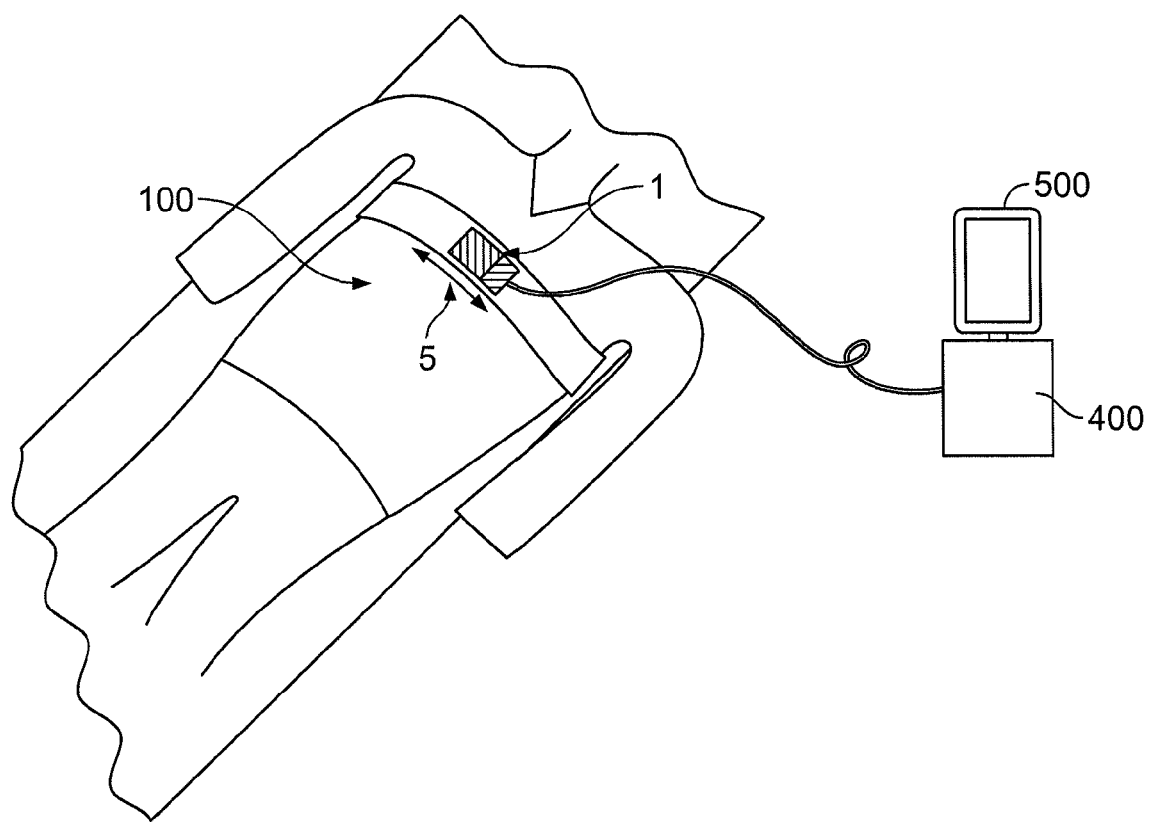
Figure 6A:
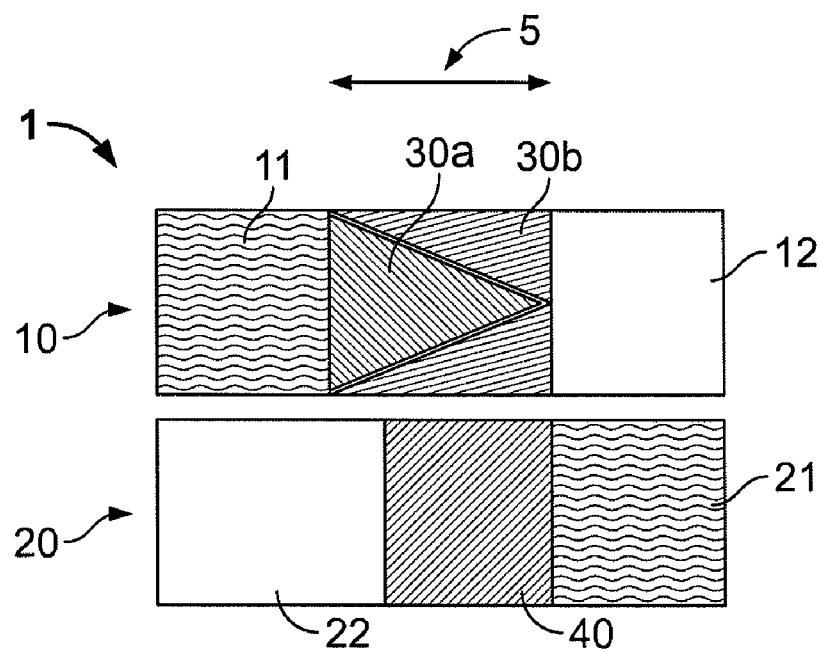
Figure 6B:
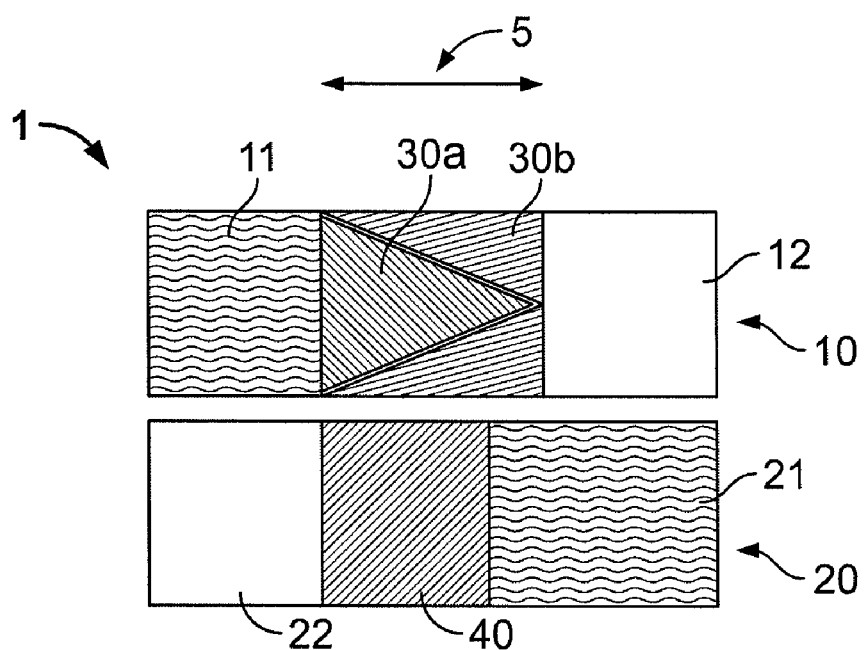
Figure 7:
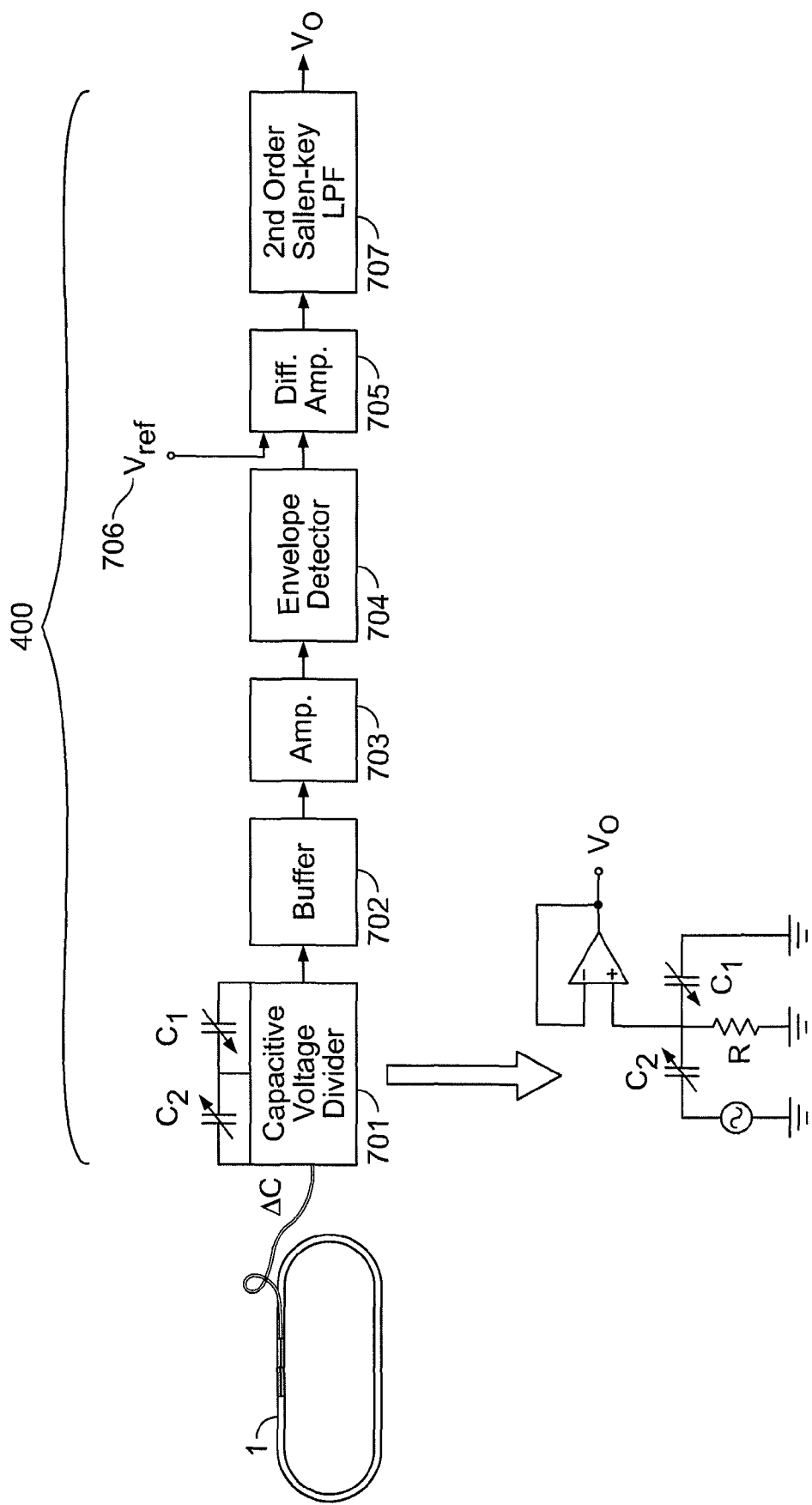
Figure 8A:
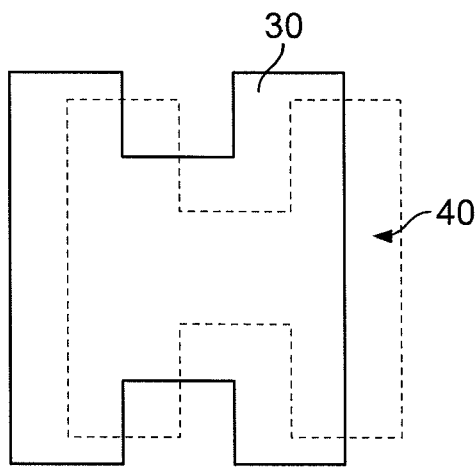
Figure 8B:
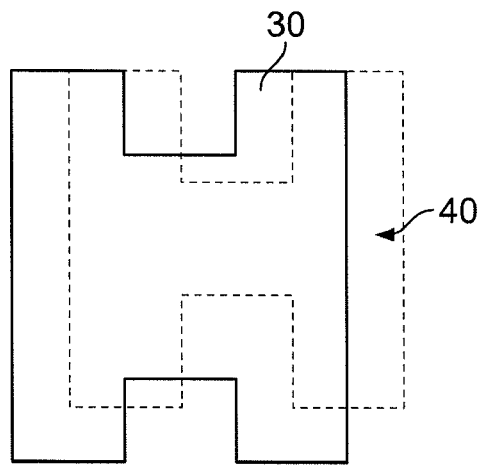
Figure 8C:
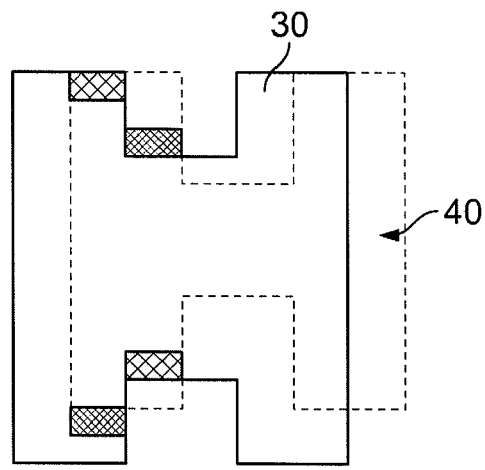
Figure 9:
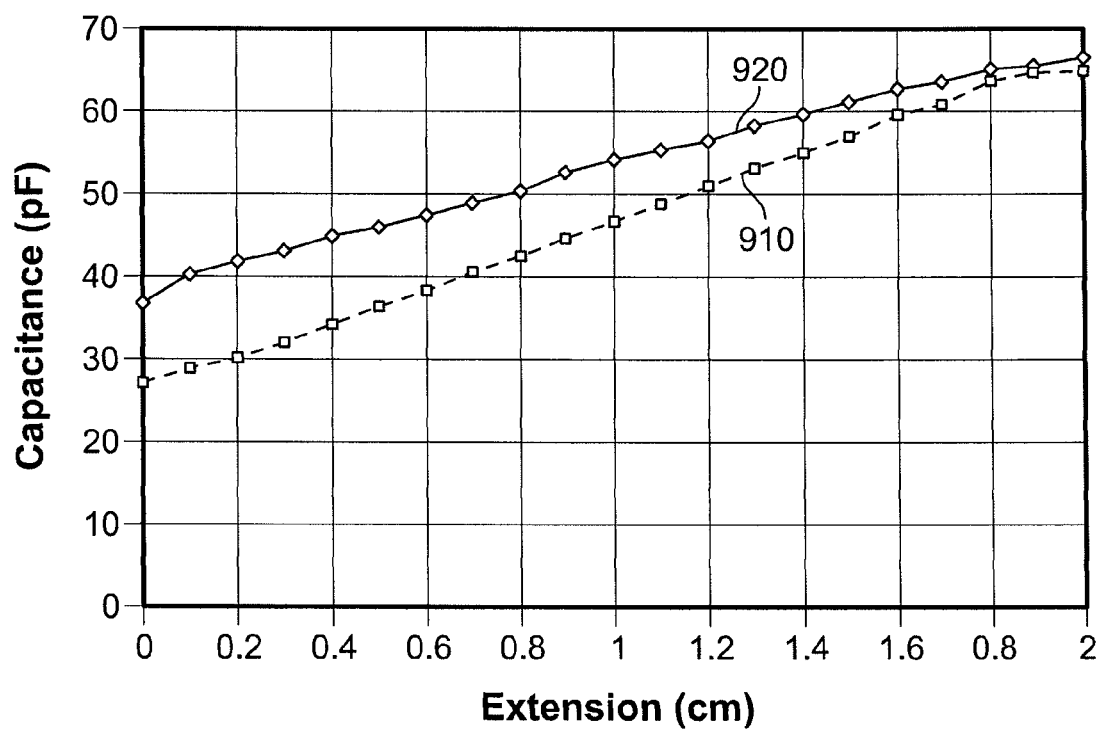

Having thus described the invention in general terms, reference will now be made to the accompanying drawings, which are not necessarily drawn to scale, and wherein:

FIG. 1 shows a non-limiting side-view schematic of a sensor device, according to one embodiment of the present invention;

FIG. 2A shows a non-limiting top-view schematic of the first and second fabric substrates, and corresponding first and second electrode materials disposed thereon, according to one embodiment of the present invention, wherein the sensor device is in the equilibrium (non-stretched) configuration;

FIG. 2B shows a non-limiting top-view schematic of the first and second fabric substrates, and corresponding first and second electrode materials disposed thereon, according to one embodiment of the present invention, wherein the sensor device is in the extended (stretched) configuration;

FIG. 3A shows a non-limiting top-view schematic of the first and second fabric substrates, and corresponding first and second electrode materials disposed thereon, according to one embodiment of the present invention, wherein the second electrode material comprises a pair of electrode portions arranged in a "comb" electrode pattern, and wherein the sensor device is in the equilibrium (non-stretched) configuration;

FIG. 3B shows a non-limiting top-view schematic of the first and second fabric substrates, and corresponding first and second electrode materials disposed thereon, according to one embodiment of the present invention, wherein the second electrode material comprises a pair of electrode portions arranged in a "comb" electrode pattern, and wherein the sensor device is in the extended (stretched) configuration;

FIG. 4 shows a non-limiting schematic of a transducer circuit in communication with the sensor device, according to one embodiment of the present invention;

FIG. 5 shows a non-limiting schematic of a wearable article comprising a sensor device, according to one embodiment of the present invention, wherein the wearable article extends substantially about a subject's chest to monitor respiratory function;

FIG. 6A shows a non-limiting top-view schematic of the first and second fabric substrates, and corresponding first and second electrode materials disposed thereon, according to one embodiment of the present invention, wherein the second electrode material comprises a pair of interlocking electrode portions arranged in a "V" electrode pattern, and wherein the sensor device is in the equilibrium (non-stretched) configuration;

FIG. 6B shows a non-limiting top-view schematic of the first and second fabric substrates, and corresponding first and second electrode materials disposed thereon, according to one embodiment of the present invention, wherein the second electrode material comprises a pair of interlocking electrode portions arranged in a "V" electrode pattern, and wherein the sensor device is in the extended (stretched) configuration;

FIG. 7 shows a non-limiting schematic of a transducer circuit in communication with the sensor device comprising a differential capacitive sensor, according to one embodiment of the present invention;

FIGS. 8A-8C show non-limiting top view schematics of the first and second electrode materials, wherein the first electrode material includes a height that is larger than the corresponding height of the second electrode material such that the sensor device is capable of compensating for slight misalignment of the electrode materials in a direction substantially perpendicular to the selected direction; and FIG. 9 shows a non-limiting plot of capacitance vs. extension in the selected direction for a sensor device according to one embodiment of the present invention, illustrating the substantial linearity of the capacitance vs. extension relationship of the sensor device.

DETAILED DESCRIPTION OF THE INVENTION

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

While the various embodiments of the present invention are described herein in the context of a sensor system for monitoring motion, expansion and/or contraction that may be indicative of respiratory function, it should be understood that the various system embodiments described herein may also be used to monitor motion that may be indicative of other body functions and/or medical conditions. For example, various sensor devices 1 and wearable articles described more fully herein may be used to monitor conditions that may include, but are not limited to: labor contractions in pregnancy; muscle spasms and/or contractions; joint motion and/or range of motion in extremities; and other conditions that may be monitored and/or assessed by the detection of movement, expansion, and/or contraction in a structure 100 about which a garment may be worn. It should be further understood that the various sensor device 1 embodiments described herein may be useful in monitoring respiration in a user and/or emitting an alert signal when respiratory function (and/or movement that is indicative thereof) ceases and/or significantly changes. Thus, various sensor device 1 embodiments described herein may be useful in a number of monitoring applications including, but not limited to: infant monitoring (to aid in the prevention of sudden infant death syndrome (SIDS)); ECG monitoring; motor vehicle driver monitoring; pilot monitoring; and/or patient monitoring in a clinical and/or home care setting.

It should further be understood that the various sensor device 1 embodiments described herein utilize capacitive sensors to measure parameters related to movement of an anatomical structure (that may be indicative, for example, of respiratory function). For example, in some embodiments, as shown in FIG. 1, the sensor device 1 comprises a first electrode material 30 disposed on a first fabric substrate 10 and a second electrode material 40 disposed on a second fabric substrate 20 such that the first electrode material 30 and the second electrode material 40 are configured to cooperate to form a parallel plate capacitive sensor, as described further herein. A basic parallel plate capacitor utilizes a pair of electrical "plate" conductors (described herein as first and second electrode materials 30, 40, for example) arranged in parallel and separated by an air gap and/or a dielectric material (which, as described further herein, may comprise a spacer comprising an adhesive layer 31, 41 disposed on one or more of the first and second electrode materials 30, 40). The capacitance (C) of such a parallel plate capacitor may be expressed (in Farads (F)) by the following formula:

$$C = \frac{\varepsilon A}{d} = \frac{\varepsilon_0 \varepsilon_r A}{d} \quad (1)$$

Wherein, A is the plate area (i.e. the "overlap" in parallel plates (such as the overlap of the first and second electrode portions 30, 40, shown generally in FIG. 1)); d is the spacing between parallel plates (which may be determined, in some embodiments, by a thickness of a dielectric spacer material 31, 41 disposed between the electrode plates); $\varepsilon$ is permittivity; $\varepsilon_0$ is the dielectric constant for a vacuum (8.854 pF/m, for example); and $\varepsilon_r$ is the relative dielectric constant (which may characterize the dielectric spacer material and/or materials 31, 41 disposed between the electrode materials 30, 40 of the parallel plate capacitor). As described further herein, changes in capacitance due to changes in the effective overlap area (A) of two electrode materials disposed on fabric substrates 10, 20 may be used to effectively measure movement in an anatomical structure 100 (see FIG. 5, for example) that may be indicative of biological processes (such as respiration).

As shown generally in FIG. 1, some embodiments of the present invention provide a sensor device 1 adapted to be operably engaged with an anatomical structure 100 (see FIG. 5, for example, showing a sensor device 1 operably engaged with and/or surrounding a torso and/or chest for assessing respiratory function). In some embodiments, the sensor device comprises a first fabric substrate 10 comprising a first compliant portion 11 configured to stretch only in a selected direction 5, and a first non-compliant portion 12 configured for providing a stable non-compliant surface on which an electrode material 30, 40 may be applied. As shown in FIGS. 2A and 2B, the sensor device 1 may be configured such that as the compliant portions 11, 21 stretch in the selected direction 5, the electrode materials 30, 40 forming a capacitive sensor may move generally towards each other such that the overlap area (and corresponding capacitance) of the two electrode portions 30, 40 increases as the sensor device 1 is stretched and/or expanded.

In order to "build-up" a parallel structure suitable for creating the parallel electrode plates of a parallel plate capacitor, the sensor device 1 may further comprise a second fabric substrate 20, disposed substantially parallel to the first fabric substrate 10 such that the first and second fabric substrates 10, 20 form parallel "layers" of a sensor device 1 that may be integrated into a wearable article (such as a compliant belt, for example, as shown in FIG. 5). As shown in FIG. 1, the second fabric substrate 20 may comprise a second compliant portion 21 configured to stretch only in the selected direction 5, and a second non-compliant portion 22 configured for providing a second stable non-compliant surface on which an electrode material 30, 40 may be applied.

In various sensor device 1 embodiments, at least one of the first fabric substrate 10 and the second fabric substrate 20 may comprise a non-woven fabric that may include, but is not limited to a hydroentangled mat of fibers. In some embodiments, at least one of the first fabric substrate 10 and the second fabric substrate 20 may comprise a woven fabric and/or some combination woven and non-woven fabrics. Furthermore, in some embodiments the compliant portions 11, 21 may be operably engaged with the non-compliant portions 12, 22 in a substantially seamless lateral connection established, for example using an ultrasonic bonding process to form at least one of the first and second fabric substrates 10, 20. As described herein, the compliant portions 11, 21 comprise fabric configured to stretch in substantially only one direction (such as the selected direction 5, depicted generally in FIG. 1) such that any change in capacitance (C) in the sensor device 5 may be correlated directly to extension of the sensor (due to relative motion of the electrode portions 30, 40) in the selected direction 5. Furthermore, the non-compliant portions 12, 22 may comprise, in some embodiments, a substantially non-stretchable non-woven fabric comprising, for example a blend of 70% polyethylene terephthalate (PET) and 30% nylon.

Referring again to FIG. 1, the sensor device 1 may further comprise first and second electrode materials 30, 40 disposed on the parallel fabric substrates 10, 20 to form a parallel plate capacitor having a variable capacitance based on the change in overlap area A, that occurs as the relative positions of the electrode materials 30, 40 change as the sensor device 1 stretches (i.e. due to inhalation when the sensor device 1 is operably engaged about a patient's chest 100 or other expanding and/or contracting structure (see FIG. 5, for example)). As shown generally in FIG. 1, the sensor device 1 may comprise a first electrode material 30 disposed on the first non-compliant portion 12 and a second electrode material 40 disposed on the second non-compliant portion 22 such that the first electrode material 30 and the second electrode material 40 are configured to cooperate to form a parallel plate capacitive sensor having a variable capacitance corresponding to a relative motion of the first fabric substrate 10 and the second fabric substrate 20 as the anatomical structure 100 expands and/or contracts. In some sensor device 1 embodiments, as described further herein with respect to FIGS. 2A and 2B, for example, the variable capacitance may be configured to be variable in a substantially linear relationship to the relative motion of the first fabric substrate 10 and the second fabric substrate 20 as the anatomical structure 10 expands and stretches the sensor device 1.

In various sensor device 1 embodiments, at least one of the first electrode material 30 and the second electrode material 40 may comprise a conductive material including, but not limited to: a conductive ink; a conductive foil; and combinations of such conductive materials. The conductive material used to print and/or prepare the electrode materials 30, 40 may include, but is not limited to: silver (such as, for example, silver ink CMI 112-15, commercially available from Creative Materials, Inc. of Tyngsboro, Mass.); gold; copper; aluminum; and/or combinations of such conductive materials. In some embodiments, wherein at least one of the first and second electrode materials 30, 40 comprise a conductive ink, the conductive ink may be screen printed on at least one of the first non-compliant portion 12 and the second non-compliant portion 22 in order to form the parallel plate capacitor structure shown generally in FIG. 1 (which, as described herein, may exhibit a linearly variable capacitance in relation to a stretch and/or relative displacement of the compliant portions 11, 21 of the first and second fabric substrates 10, 20 in the selected direction 5).

Furthermore, and as shown generally in FIG. 1, some sensor device 1 embodiments may further comprise a first insulating layer 32 disposed between the first electrode material 30 and the first non-compliant portion 12 and a second insulating layer 42 disposed between the second electrode material 40 and the second non-compliant portion 22. Such insulating layers 32, 42 may act to electrically insulate the outer surfaces of the parallel plate capacitor structure and may also be configured for coating the non-compliant portions 12, 22 of the fabric substrates 10, 20 such that conductive ink or other electrode materials 30, 40 may be prevented from penetrating the fabric substrates 10, 20 (the use of insulating layers 32, 42 may be especially useful in sensor device 1 embodiments wherein the electrode materials 30, 40 are screen printed on one or more of the first and second non-compliant portions 12, 22, respectively).

In some alternate sensor device 1 embodiments wherein at least one of the first and second electrode materials 30, 40 comprises a conductive foil, the conductive foil may be operably engaged with at least one of the first non-compliant portion 12 and the second non-compliant portion 22 using an adhesive coating (see elements 31 and 41, respectively, for example) disposed on the conductive foil and overlapping onto at least a portion of at least one of the first non-compliant portion 12 and the second non-compliant portion 22. For example, in some sensor device 1 embodiments, at least one of the first and second electrode materials 30, 40 may comprise an aluminum foil attached to at least one of the non-compliant portions 12, 22 using an adhesive over-layer. As described further herein, an adhesive over-layer (shown, for example, as elements 31 and 41 in FIG. 1) may not only serve to adhere the electrode materials 30, 40 to the non-compliant portions 12, 22 of the fabric substrates 10, 20, but may also act as a dielectric spacing layer disposed between the parallel "plates" formed by the electrode materials 30, 40. The thickness of such a dielectric spacer material 31, 41 disposed between the first electrode material 30 and the second electrode material 40 may determine, for example, the distance (d) between the "plates" of the parallel plate capacitor that, in turn, may determine the capacitance output of the sensor device (see Equation (1) herein). In various embodiments, the dielectric spacing material 31, 41 may comprise an adhesive coating (i.e. an "over-layer") disposed on at least one of the first electrode material 30 and the second electrode material 40.

Referring again to FIG. 1, some sensor device 1 embodiments may further comprise a shield 50 disposed on a side of the first fabric substrate 10 opposite the first electrode material 30. The shield 50 may be configured for shielding at least one of the first electrode material 30 and the second electrode material 40 from one or more stray electric fields originating from outside the sensor device 1. Also as shown in FIG. 1, the sensor device 1 may also comprise a shield 50 disposed on a side of the second fabric substrate 20 opposite the second electrode material 40. The shield 50 may also be configured to reduce "fringe" effects or "back plane" effects resulting from charge distributions (and resulting stray electric fields) on the "back side" (i.e. outside the parallel plate capacitor structure) of the electrode materials 30, 40 and, more specifically, on the back side of portions of the electrode materials 30, 40 that do not overlap to form the area (A) of the parallel plate capacitor at any given length of the sensor device 1. Thus, as the sensor device 1 stretches (see FIG. 2B, for example) and consequently, as the overlap area (A) decreases (such that the free or non-overlapping portions of the electrode materials 30, 40 increases), the linearity of the variable capacitance vs. stretch in the selected direction 5 may be compromised due to fringe effects originating on portions of the electrode materials 30, 40 that are not overlapping at any given point in the extension and/or retraction of the sensor device 1.

The shield 50 may comprise, for example, a conductive electrode configured for modifying and/or negating the distorted electric fields created by the "fringe" and/or "back plane" effects so as to increase the linearity of the sensing range of the sensor device 1. The shield 50 may also serve to protect the electrode materials 30, 40 from electrically-coupled noise. As shown generally in FIG. 1, the shield 50, in some sensor device 1 embodiments, may be placed in parallel with the first and second electrode materials 30, 40 so as to "cover" the conductive electrode materials 30, 40 of the sensor device 1. The potential of the shield 50 may be tied to electrical ground 3 and/or tied to a potential of one or more of the first and second electrode materials 30, 40 via an operational amplifier (op-amp) 4. More specifically, in some sensor device 1 embodiments, the shield 50 may be in communication with an electrical ground 3. In other alternative sensor device 1 embodiments, the sensor device 1 may further comprise an op-amp 4 operably engaged between the shield 50 and at least one of the first and second electrode materials 30, 40.

FIGS. 2A and 2B show a "top view" of the first and second fabric substrates 10, 20 (and the first and second electrode materials 30, 40 operably engaged with first and second non-compliant portions 12, 22, respectively) in both the equilibrium (non-stretched) (FIG. 2A) and the extended (stretched) (FIG. 2B) positions. It should be understood that any specific dimensions set forth in the drawings (such as FIGS. 2A, 2B, 3A and 3B, for example) are exemplary only and should not be construed and/or implied as limitations. As described herein, the compliant portions 11, 21 of the fabric substrates 10, 20 are configured for stretching only in the selected direction 5. By constructing a sensor device 1 embodiment wherein the plates (i.e. the electrode materials 30, 40) of a parallel plate capacitor are disposed on the non-compliant portions 12, 22 of a fabric substrate 10, 20 also having a compliant portion 11, 21, the overlap area (A) of the electrode materials 30, 40 (and consequently the capacitance (C) (see Equation (1))) is a function of the specific geometry of the electrode materials 30, 40 and the stretched length of the sensor device 1 in the selected direction 5.

In some sensor device 1 embodiments, the shapes of the conductive areas 30, 40 may be designed to ensure that overlap of the electrode materials 30, 40 (resulting in the area (A) of the parallel plate capacitor), varies substantially linearly with the stretched length of the sensor device 1 in the selected direction 5, within the area limits of the sensor device 1 (denoted below as a minimum area ($A_{min}$) and a maximum area ($A_{max}$)). For example, as shown in FIGS. 2A and 2B the conductive areas 30, 40 forming the "plates" of a variable-capacitance parallel plate capacitor may be screen printed or otherwise operably engaged with the fabric substrates 10, 20 in a substantially "H-shape" pattern comprising "vertical bars" and connecting "horizontal bars." For example, as shown in FIGS. 2A and 2B at least one of the first electrode material 30 and the second electrode materials 40 may be disposed on the corresponding non-compliant portion 12, 22 in a corresponding at least one of a first H-shape and a second H-shape. In such embodiments, the first and second H-shapes may comprise at least a pair of vertical bars extending substantially perpendicularly to the selected direction 5, the vertical bars including a width ($w_4$, for example) and a height (h, for example). The H-shapes may further comprise at least one horizontal bar extending substantially parallel to the selected direction 5, the horizontal bar including a width ($w_5$, for example) and a height ($h_1$, for example).

Referring to FIGS. 2A and 2B, the sensor device 1 embodiments of the present invention may be designed to ensure that the capacitance (C) between the two electrode materials 30, 40 increases substantially linearly (see FIG. 9, for example) as the sensor device 1 stretches (due to the extension of the compliant portions 11, 21, for example) in the selected direction 5. In some embodiments, the width ($w_4$, for example) of the vertical bars may be substantially equivalent to a change in a length of the first and second compliant portions 11, 21 when stretched substantially completely (see FIG. 2B, for example) in the selected direction 5. For example, in some embodiments, wherein the compliant portions 11, 21 are configured for stretching in length (i.e. in the selected direction 5) to 140% of its original length at equilibrium (see FIG. 2A, for example), then the widths ($w_4$, $w_6$ for example) of the vertical bars of the electrode materials 30, 40 should be set at 40% of the "at-rest" length ($w_1$ (see FIG. 2A)) of the compliant portions 11, 21 to ensure substantially linear variations in capacitance. Furthermore, to ensure continuity in such embodiments, the width ($w_5$, for example) of the horizontal bars (corresponding to spacing between the adjacent vertical bars) should also be set at 40% of the "at-rest" length ($w_1$ (see FIG. 2A)) of the compliant portions 11, 21. For example, as shown in FIGS. 2A and 2B, if the dimension $w_1$ of the compliant portions 11, 21 is 5 cm in the equilibrium position (see FIG. 2A), then the corresponding width $w_4$ of the vertical bars (and the spaces therebetween defined by $w_5$, for example) should be set at or about 2 cm to ensure linearity in the capacitance output of the sensor device 1.

As shown in FIGS. 8A-8C, in some sensor device 1 embodiments, the relative heights of the vertical and/or horizontal bars forming at least one of the first and second electrode materials 30, 40 may be greater than the corresponding height of the vertical bars and the height of the horizontal bars of the other of the first and second H-shapes such that the variable capacitance is variable in a substantially linear relationship to the relative motion of the first fabric substrate and the second fabric substrate as the anatomical structure expands. For example, in some embodiments, the heights of the vertical and horizontal bars making up the first H-shape may be substantially about 50% larger that the corresponding heights of the vertical and horizontal bars making up the second H-shape. In some other embodiments, the heights of the vertical and horizontal bars making up the first H-shape may be substantially about 100% larger that the corresponding heights of the vertical and horizontal bars making up the second H-shape.

As shown in FIGS. 8B and 8C the height differential between the first and second electrode materials 30, 40 may allow the capacitance value generated by the sensor device 1 to remain substantially linear (see FIG. 9, for example, showing an exemplary plot of capacitance (C) vs. extension of a sensor device 5 according to one embodiment) over the extension length in the selected direction 5 regardless of slight misalignment of the first and second electrode materials 30, 40 in a direction that is substantially perpendicular to the selected direction 5 (i.e., the direction of extension). Thus, the configuration and dimensions of the electrode materials 30, 40 shown in the exemplary embodiment of FIGS. 8A-8C may allow the sensor device 1 to compensate for slight misalignment in the directions perpendicular to the selected (extension) direction 5 that may result from slight manufacturing defects and/or the variability that may be inherent in a sensor device 1 that is embedded in and/or operably engaged with a fabric substrate 10, 20. Furthermore, as shown generally in the schematic view of FIG. 8C (including cross-hatching showing (1) overlap area gains, and (2) overlap area reductions) the shapes of the electrode materials 30, 40 may be configured for providing a substantially equal variation in area (and corresponding variation in capacitance) regardless of slight misalignment of the electrode materials 30, 40 in a direction substantially perpendicular to the selected direction 5.

According to the exemplary sensor device 1 embodiments shown generally in FIGS. 2A and 2B, the formulas for calculating the conductive area (A) of the parallel plate capacitor formed by the electrode materials 30, 40 may be expressed as:

$$A_{var} = (N+1)w_4 h_1 + Nw'(h-h_1)$$
$$A_{min} = (N+1)w_4 h_1 \quad (2)$$
$$A_{max} = (N+1)w_4 h_1 + Nw_4(h-h_1)$$

Where N indicates the number of "vertical bars" in the overlapping sensor area (A), and where w' is the maximum "stretched" length of the sensor device 1. For the purposes of this example, the width ($w_4$, $w_6$) of the "vertical bars" of the conductive materials 30, 40 shown in FIGS. 2A and 2B are assumed to be substantially equal. Because, the overlapping area (A) of the conductive materials 30, 40 increases linearly along the selected direction 5 as the sensor device 1 is stretched (see FIG. 2B showing "full extension," for example), the variations in linear capacitance (C) resulting from the changes in conductive area (A) (see Equation (2)) may be expressed as follows:

$$C_{var} = \frac{\varepsilon A_{var}}{d} = \frac{\varepsilon[(N+1)w_4 h_1 + Nw'(h-h_1)]}{d} \quad (3)$$
$$C_{min} = \frac{\varepsilon A_{min}}{d} = \frac{\varepsilon(N+1)w_4 h_1}{d}$$
$$C_{max} = \frac{\varepsilon A_{max}}{d} = \frac{\varepsilon[(N+1)w_4 h_1 + Nw_4(h-h_1)]}{d}$$

Where $\varepsilon$ is the permittivity of a dielectric spacer material 31, 41 disposed between the electrode materials 30, 40, and d is the distance between the electrode materials 30, 40 forming the "plates" of the variable capacitance parallel plate capacitor. The variation in capacitance (C) of the sensor device 1 may thus depend substantially only on the change in length of the sensor device 1 in the selected direction 5 and on the number of "vertical bars" or other area elements making up the area of the electrode materials 30, 40 on the first and second non-compliant portions 12, 22 of the fabric substrates 10, 20. Thus, in the exemplary embodiment shown in FIGS. 2A and 2B the sensor device 1 exhibits minimum capacitance when the sensor device 1 is in the equilibrium position (see FIG. 2A). The dimensions of the conductive "horizontal bars" ($h_1$), orthogonal to the selected direction 5, ensures in some embodiments, a minimum capacitance resulting from the "horizontal" portions of the electrode materials 30, 40 regardless of the stretched length of the sensor device 1. Thus, only those dimensions in the selected direction 5 substantially change the capacitance of the sensor device 1 by altering the overlapping areas of the electrode materials 30, 40 as the sensor device 1 stretches and/or relaxes to the equilibrium position (see FIG. 2A, for example).

It should be understood that the sensitivity of the exemplary embodiment of the sensor device 1 shown in FIGS. 2A and 2B may be expressed as:

$$\text{Sensitivity} = \frac{\partial C_{var}}{\partial w'} = \frac{N(h-h_1)}{d}. \quad (4)$$

The exemplary embodiment of the sensor device 1 shown generally in FIGS. 2A and 2B may provide substantially the same capacitance output regardless of whether the applied stretching load (applied, for example, in the selected direction 5) is increasing (stretching) or decreasing (relaxing) along the selected direction 5.

In some alternative embodiments, as shown generally in FIGS. 3A and 3B, the sensor device 1 may be configured as a differential capacitive sensor. For example, the first electrode material 30 may comprise a first electrode portion 30a and a second electrode portion 30b such that the second electrode material 40, the first electrode portion 30a, and the second electrode portion 30b are configured to cooperate to form a differential capacitive sensor having a variable capacitance established between the second electrode material 40 and at least one of the first electrode portion 30a and the second electrode portion 30b corresponding to the relative motion of the first fabric substrate 10 and the second fabric substrate 20 as the anatomical structure 100 expands and/or contracts. As shown in FIGS. 3A and 3B the first electrode portion 30a and the second electrode portion 30b may be disposed in a substantially interlocking configuration to form a comb electrode. In some alternative sensor device 1 embodiments, as shown generally in FIGS. 6A and 6B, the first and second electrode portions 30a, 30b may be disposed in a substantially interlocking "V" configuration on the first fabric substrate 10.

The differential capacitive sensor device 1 shown generally in FIGS. 3A, 3B, 6A, and 6B may reduce potential static interference effects in a fabric-based sensor device 1 (that may arise, for example, from moisture and/or shrinkage of the fabric substrates 10, 20). In such embodiments, the sensor device 1 comprises two separate variable capacitors as follows: (1) a first capacitor established between the second electrode material 40 and the first electrode portion 30a; and (2) a second capacitor established between the second electrode material 40 and the second electrode portion 30b. The two variable capacitors may combine to "cancel out" interference effects as described herein. In such embodiments, the second electrode material 40 serves as a "pickup plate" that is movable laterally with respect to the two electrode portions 30a, 30b, such that the capacitance of each capacitor element varies equally whether the pickup plate moves to the left or to the right in the selected direction 5.

As shown in FIGS. 3A and 3B some differential capacitive sensor device 1 embodiments may comprise a first electrode material 30 divided into first and second electrode portions 30a, 30b disposed in an interlocking "comb" electrode configuration. As described further herein, such a "comb" configuration may provide a substantially linear capacitance versus extension curve due to the linear duplicated area change provided by the interlocking tines of the "comb." In some such "comb" differential capacitive sensor device 1 embodiments at least one of the first electrode portion 30a and the second electrode portion 30b may comprise at least two vertical bars extending substantially perpendicularly to the selected direction 5; and at least one horizontal bar extending substantially parallel to the selected direction 5. As shown in FIGS. 3A and 3B, the at least one horizontal bar may be operably engaged between the at least two vertical bars to form a portion 30a, 30b of the comb electrode. Furthermore in such embodiments, the second electrode material 40 may be disposed as a substantially rectangular frame on the second non-compliant portion 22. As shown in FIG. 3A the substantially rectangular frame shape of the second electrode material 40 may define a substantially rectangular aperture therein. As described further herein, the resulting differential areas and corresponding differential capacitances in such embodiments are governed by the equations (5) through (9) listed herein.

However, on comparatively large flexible fabric substrates 10, 20 in may be difficult to maintain plate-to-plate distance (d) between the pickup plate (i.e. the second electrode material 40) and at least one of the first and second electrode portions 30a, 30b, due to bending and/or tilting of the fabric substrates 10, 20 as they encircle and/or partially surround the anatomical structure 100. This may result in unbalanced capacitance variance. Thus, as shown in FIGS. 6A and 6B, some differential capacitive sensor device 1 embodiments may comprise a first electrode material 30 divided into first and second electrode portions 30a, 30b disposed in an interlocking "V" electrode configuration. The interlocking "V" formed by the first and second electrode portions 30a, 30b may provide a more consistent space and/or distance (d) between the pickup plate (embodied herein as the second electrode material 40) and the two electrode portions 30a, 30b. The trade-off in such embodiments, however, is that the "V" electrode configuration may not produce variations in capacitance (C) that vary substantially linearly as the sensor device 1 is stretched along the selected direction 5.

Some differential capacitive sensor embodiments (as shown in FIGS. 3A and 3B) consist of two variable parallel plate capacitors comprising: (1) a first capacitor defined between elements 30a and 40 and; (2) a second capacitor defined between elements 30b and 40. These capacitors are arranged such that they provide the same variation in capacitance regardless of which direction the fabric substrates 10, 20 move relative to one another during a stretching and/or relaxation cycle of the overall sensor device 1 structure. For example, as shown in FIGS. 3A and 3B, if the second electrode material 40 moves laterally with respect to the first and second electrode portions 30a and 30b then the capacitance of each capacitor portion varies equally whether it moves to the right or to the left in the selected direction 5.

$$A_{30b} = (N+1)w_4h_2 + N(w_4-w')h_1 \quad (5)$$

$$A_{30a} = (N+1)w_4h_2 + Nw'h_1$$

It should be understood that w' refers to the stretched length of the sensor device 1. The overlapping areas (A) for each capacitor portion change between minimum and maximum ($A_{min}$ and $A_{max}$) area values as the sensor device 1 expands and contracts. Thus, the minimum and maximum area values may be expressed as:

$$A_{min} = (N+1)w_4h_2 \quad (6)$$

$$A_{max} = (N+1)w_4h_2 + Nw_4h_1$$

Therefore, referring to Equation (1), the corresponding capacitances (C) may be expressed as:

$$C_{30b} = \frac{\varepsilon[(N+1)w_4h_2 + N(w_4-w')h_1]}{d} \quad (7)$$

$$C_{30a} = \frac{\varepsilon[(N+1)w_4h_2 + Nw'h_1]}{d}$$

Where d is the distance between the second electrode material 40 and at least one of the two electrode portions 30a, 30b. Also, the minimum and maximum capacitance values are given by:

$$C_{min} = \frac{\varepsilon[(N+1)w_4h_2]}{d} \quad (8)$$

$$C_{max} = \frac{\varepsilon[(N+1)w_4h_2 + Nw_4h_1]}{d}$$

As can be seen when reviewing Equations (8) in light of FIGS. 3A and 3B, the second electrode portion 30b has maximum capacitance and the first electrode portion 30a has minimum capacitance when the sensor device 1 is in the equilibrium state (relaxed) as shown in FIG. 3A, for example. As the sensor device 1 stretches in the selected direction 5, the capacitance values at each electrode portion change linearly in opposing directions. Furthermore, if the sensor device 1 stretches fully to the extended position (see FIG. 3B), then the first electrode portion 30a (in cooperation with the second electrode material 40) creates a maximum capacitance value and the second electrode portion 30b (in cooperation with the second electrode material 40) creates a minimum capacitance. Furthermore, it should be understood that the sensitivity of each capacitor portion formed by each corresponding electrode portion 30a and 30b, may be expressed as:

$$Sensitivity_{30b} = \frac{\partial 30b}{\partial w'} = \frac{-Nh_1}{d} \quad (9)$$

$$Sensitivity_{30a} = \frac{\partial 30a}{\partial w'} = \frac{Nh_1}{d}$$

As shown in FIG. 4, some sensor device 1 embodiments may further comprise a transducer circuit 400 in communication with the parallel plate capacitive sensor. The transducer circuit 400 may be configured for converting the variable capacitance into corresponding variable voltage indicative of the expansion and/or contraction of the anatomical structure 100. Referring again to FIG. 4, the transducer circuit 400 may be configured for conditioning waveforms, for example respiratory function signals, being generated by the sensor device 1. For example, in some embodiments, the sensor device 1 may be configured for operably engaging (i.e. wrapping substantially about) an anatomical structure 100 such as a patient's torso or chest. In some such embodiments, the transducer circuit 400 may be configured for converting the variable voltage into an indication of respiratory function corresponding to the expansion and/or contraction of the torso 100.

In some embodiments, as shown in FIG. 4, the transducer circuit 400 may comprise an RLC "tank" oscillator or other detector circuit 401 configured for converting the variable capacitance into a corresponding frequency shift. The detector circuit 401 may comprise, for example, a CMOS 7555 timer with a resistor R and capacitor C wherein the output frequency may be characterized as 1/RC and the duty cycle is substantially about 50%. Referring again to FIG. 4, the transducer circuit 400 may further comprise a buffer amplifier 402 in communication between the detector circuit 401 and the load (see elements 403-406, for example) to ensure that the output frequency of the detector circuit 401 is substantially stable. The transducer circuit 400 (as shown, for example, in FIG. 4) may further comprise an FM demodulator 403 configured for detecting the frequency shift output of the detector circuit 401. The transducer circuit 400 further comprises a low-pass filter (LPF) 404 and a differential amplifier (with gain) 405 configured for maintaining substantially flat transducer circuit 400 output signal when the sensor device 1 detects a cessation in structure function (as indicated by a lack of relative movement of the electrode materials 30, 40 within the sensor device 1). Finally, in some embodiments, the transducer circuit 400 may also comprise a second LPF 406 configured for removing unwanted noise through the signal track that may interfere with the signal sent to an alarm or other monitoring user interface 500 (see FIG. 5, for example).

In some alternate embodiments, for example wherein the sensor device 1 comprises a differential capacitive sensor (such as that shown in FIGS. 3A and 3B); the transducer circuit 400 may be modified for conditioning a differential capacitance signal into a detectable output signal. For example, as shown generally in FIG. 7, the transducer circuit 400 may comprise an analog capacitive voltage divider circuit 701 configured for generating output signals having amplitudes that are controlled by the dual capacitances generated by the differential capacitive sensor (comprising, the second electrode material 40 and the first and second electrode portions 30a, 30b). In such embodiments, the transducer circuit 400 further comprises a buffer amplifier 702 in communication between the capacitive voltage divider circuit 701 and the load (see elements 703-707, for example). As shown in FIG. 7, the transducer circuit may also comprise an amplifier 703 configured to provide an amplified output to an envelope detector circuit 704 (which may comprise, in some embodiments, a half-wave rectifier, configured for extract amplitude levels of the AC signal generated by the sensor device 1. The transducer circuit 400 may also comprise a differential amplifier 705 configured for comparing the envelope signal (the output of the envelope detector circuit 704, for example) to a reference voltage 706. In some embodiments, the transducer circuit may also comprise an LPF 707 (such as a $2^{nd}$ Order Sallen-Key LPF, for example) configured for filtering high-frequency noise from the output signal of the transducer circuit 400.

As shown generally in FIG. 5, the sensor device 100 may comprise a substantially flexible belt or strap that may be in wired and/or wireless communication with the transducer circuit 400 (and/or a processor device comprising various components of the transducer circuit 400 (as shown in FIG. 4, for example). The transducer circuit 400 may be in further communication with a user interface 500 configured for displaying a visual indication of structure function and/or an audible indication when the parameter being measures drifts out of range. In some embodiments, wherein the sensor device 1 is intended for use in patient respiratory monitoring and/or infant monitoring for the prevention of SIDS, the sensor device 1 may be in communication with the transducer circuit 400 which may, in turn, be in communication with a user interface 500 configured for generating an audible alarm when motion detected by the sensor device 1 indicates a substantial pause in respiratory function and/or a significant reduction in respiratory rate and/or intensity.

As described herein, the various sensor device 1 embodiments of the present invention provide a stable, accurate, and substantially linear capacitive sensor that may be directly integrated into wearable articles that may be worn by a patient being monitored. Thus the sensor device 1 may be unobtrusively worn by a patient or subject without the need for electrodes or other transducer components to be adhered to the skin. For example, the first fabric substrate 10 and the second fabric substrate 20 may be formed into various fabric layers of a wearable article such that as the article stretches in the selected direction 5 (see FIG. 5, for example) the sensor device 1 integrated therein may accurately and precisely detect a substantially linear change in capacitance (C) experienced by the sensor device 1 as it stretches and/or relaxes. According to such embodiments, the wearable article may include, but is not limited to: a belt extending substantially about the anatomical structure (see FIG. 5, for example); a shirt; a bandage comprising at least one adhesive material disposed thereon for operably engaging the bandage with the anatomical structure; and combinations of such wearable articles.

FIG. 9 shows simulation results for two separate sensor device 1 designs. For example, curve 920 shows a plot of capacitance (in picoFarads) versus extension (in cm) of a sensor device 1 such as that shown generally in FIGS. 2A and 2B. In addition, curve 910 shows a plot of capacitance (in picoFarads) versus extension (in cm) of a sensor device 1 such as that shown in FIGS. 8A-8C wherein one of the electrode materials 30, 40 is characterized by a larger height of the vertical and horizontal bars making up an "H-shape" electrode configuration. As can be seen from the plots in FIG. 9, the output capacitance for both embodiments increases in a substantially linear relationship to the extension of the sensor device 1. Because the sensor device 1 embodiment described herein with respect to FIGS. 8A-8C is more likely to adapt to and/or correct for misalignment of the electrode materials 30, 40 as the sensor device 1 extends, this embodiment may also be more likely to provide a capacitance output that is generally more sensitive to changes in extension. This result is shown, for example, by comparing the plots 910 and 920.

Referring again to FIG. 9, it should also be understood that the sensor device 1 design of FIGS. 2A and 2B (the response of which is shown in plot 920) generates generally more capacitance output but with less sensitivity to changes in extension of the sensor device 1. As described above, this result may be due to the fact that the electrode material 30, 40 design of FIG. 2A has less overlapped area between the first and second electrode materials 30, 40 and therefore somewhat less "room for error" when adapting to misalignment of the electrode materials 30, 40 in a direction substantially perpendicular to the selected direction 5 of extension.

The present invention also provides various method embodiments for measuring respiratory function. For example, one such method embodiment comprises a step for engaging a pair of electrodes 30, 40 with an overlapping pair of fabric substrates 10, 20 to form a sensor device 1 comprising a parallel plate capacitor. According to such embodiments, each of the fabric substrates 10, 20 may comprise a compliant portion 11, 21 configured for stretching only in a selected direction. The method further comprises wrapping the sensor device 1 substantially about an anatomical structure 100 (such as a patient's chest, for example, as shown generally in FIG. 5). The method further comprises steps for: sensing a change in capacitance in the parallel plate capacitor corresponding to stretching of the compliant portions 11, 21 due at least in part to an expansion and/or contraction of the anatomical structure 100; and converting the sensed change in capacitance to a signal indicative of the respiratory function, using a processing element (such as a circuit 400 (see FIGS. 4 and 6, for example) in communication with the sensor device 1.

Many modifications and other embodiments of the inventions set forth herein will come to mind to one skilled in the art to which these inventions pertain having the benefit of the teachings presented in the foregoing descriptions and the associated drawings. For example, any physical structure that exhibits expansion and/or contraction can serve as the structure being monitored for relative movement. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A strain-sensing device adapted to be operably engaged with a stretching or shrinking structure for assessing the movement thereof, the strain-sensing device comprising a first fabric substrate comprising a first non-compliant portion and a first compliant portion that is positioned to stretch only in a selected direction;

a second fabric substrate disposed substantially parallel to the first fabric substrate, the second fabric substrate comprising a second non-compliant portion and a second compliant portion that is positioned to stretch only in the selected direction;

a first electrode material disposed on the first non-compliant portion; and a second electrode material disposed on the second non-compliant portion such that the first electrode material and the second electrode material are positioned to cooperate to have an area of overlap that forms a parallel plate capacitive sensor having a variable capacitance corresponding to changes in the area of overlap of the first and second electrode materials that results from relative motion of the first fabric substrate and the second fabric substrate as the structure stretches or shrinks.

2. A strain-sensing device according to claim 1, wherein the first electrode material and the second electrode material comprise first H-shape and a second H-shape, each of the first and second H-shapes comprising:
at least a pair of vertical bars extending substantially perpendicularly to the selected direction, the vertical bars including a width and a height; and
at least one horizontal bar extending substantially parallel to the selected direction, the horizontal bar including a width and a height.

3. A strain-sensing device according to claim 2, wherein the height of the vertical bars and the height of the horizontal bars of the first H-shape is greater than the corresponding height of the vertical bars and the height of the horizontal bars of the second H-shape such that the variable capacitance is variable in a substantially linear relationship to the relative motion of the first fabric substrate and the second fabric substrate as the structure stretches.

4. A strain-sensing device according to claim 2, wherein the width of the vertical bars is equivalent to a change in a length of the first and second compliant portions when stretched completely in the selected direction.

5. A strain-sensing device according to claim 1, wherein first electrode material comprises a first electrode portion and a second electrode portion such that the second electrode material, the first electrode portion, and the second electrode portion are positioned to cooperate to form a differential capacitive sensor having a variable capacitance established between the second electrode material and at least one of the first electrode portion and the second electrode portion corresponding to the relative motion of the first fabric substrate and the second fabric substrate as the structure being measured stretches or shrinks.

6. A strain-sensing device according to claim 5, wherein the first electrode portion and the second electrode portion are disposed in a substantially interlocking configuration to form a comb electrode.

7. A strain-sensing device according to claim 6, wherein at least one of the first electrode portion and the second electrode portion comprise:
at least two vertical bars extending substantially perpendicularly to the selected direction; and
at least one horizontal bar extending substantially parallel to the selected direction, the at least one horizontal bar being operably engaged between the at least two vertical bars to form a portion of the comb electrode.

8. A strain-sensing device according to claim 7, wherein the second electrode material is disposed as a substantially rectangular frame on the second noncompliant portion, the substantially rectangular frame defining a substantially rectangular aperture therein.

9. A strain-sensing device according to claim 7, wherein the width of the vertical bars is equivalent to a change in a length of the first and second compliant portions when stretched substantially completely in the selected direction.

10. A strain-sensing device according to claim 1, wherein the capacitance is variable in a substantially linear relationship to the relative motion of the first fabric substrate and the second fabric substrate as the structure being measured stretches or shrinks.

11. A strain-sensing device according to claim 1, wherein at least one of the first fabric and the second fabric substrate comprise a woven fabric.

12. A strain-sensing device according to claim 1, wherein at least one of the first fabric substrate and the second fabric substrate comprise a non-woven fabric.

13. A strain-sensing device according to claim 12, wherein the non-woven fabric comprises a hydroentangled non-woven fabric.

14. A strain-sensing device according to claim 1, wherein the first compliant portion and the first non-compliant portion are ultrasonically bonded to form the first fabric substrate.

15. A strain-sensing device according to claim 1, wherein the second compliant portion and the second non-compliant portion are ultrasonically bonded to form the second fabric substrate.

16. A strain-sensing device according to claim 1, wherein at least one of the first electrode material and the second electrode material comprise a conductive material selected from the group consisting of:
a conductive ink;
a conductive foil; and
combinations thereof.

17. A strain-sensing device according to claim 16, wherein the conductive ink is screen printed on at least one of the first non-compliant portion and the second noncompliant portion.

18. A strain-sensing device according to claim 16, wherein the conductive foil is operably engaged with at least one of the first non-compliant portion and the second non-compliant portion using an adhesive coating disposed on the conductive foil and overlapping onto at least a portion of at least one of the first non-compliant portion and the second non-compliant portion.

19. A strain-sensing device according to claim 1, further comprising a transducer circuit in communication with the parallel plate capacitive sensor, the transducer circuit configured for converting the variable capacitance into corresponding variable voltage indicative of the stretching or shrinking of the structure being measured.

20. A strain-sensing device according to claim 19, wherein the structure being measured includes an anatomical torso, and wherein the transducer circuit is further configured for converting the variable voltage into an indication of respiratory function corresponding to the expansion or contraction of the torso.

21. A strain-sensing device according to claim 19, wherein the transducer circuit comprises a RLC oscillator or other detecting circuit configured for converting the variable capacitance into a corresponding frequency shift.

22. A strain-sensing device according to claim 1, further comprising a shield disposed on a side of the first fabric substrate opposite the first electrode material, the shield positioned to shield at least one of the first electrode material and the second electrode material from one or more stray electric fields originating from outside the strain-sensing device.

23. A strain-sensing device according to claim 22, wherein the shield is in communication with an electrical ground.

24. A strain-sensing device according to claim 22, further comprising an operational amplifier circuit operably engaged between the shield and the first electrode material.

25. A strain-sensing device according to claim 1, further comprising a shield disposed on a side of the second fabric substrate opposite the second electrode material, the shield positioned to shield at least one of the first electrode material and the second electrode material from one or more stray electric fields originating from outside the strain-sensing device.

26. A strain-sensing device according to claim 25, wherein the shield is in communication with an electrical ground.

27. A strain-sensing device according to claim 25, further comprising an operational amplifier circuit operably engaged between the shield and the first electrode material.

28. A strain-sensing device according to claim 1, further comprising a dielectric spacer material disposed between the first electrode material and the second electrode material.

29. A strain-sensing device according to claim 28, wherein the dielectric spacer material comprises an adhesive coating disposed on at least one of the first electrode material and the second electrode material.

30. A strain-sensing device according to claim 1, further comprising:
   a first insulating layer disposed between the first electrode material and the first non-compliant portion; and
   a second insulating layer disposed between the second electrode material and the second non-compliant portion.

31. A strain-sensing device according to claim 1, wherein the first fabric substrate and the second fabric substrate are formed into a wearable article.

32. A strain-sensing device according to claim 31, wherein the wearable article is selected from the group consisting of:
   a belt extending substantially about the structure;
   a shirt;
   a bandage comprising at least one adhesive material disposed thereon for operably engaging the bandage with the structure; and
   combinations thereof.

33. A method for measuring a respiratory function using a strain sensor, the method comprising
   engaging a pair of electrodes with an overlapping pair of fabric substrates to form a strain-sensing device comprising a parallel plate capacitor, each of the fabric substrates comprising a compliant portion positioned for stretching only in a selected direction;
   wrapping the strain-sensing device substantially about an anatomical structure;
   sensing strain by a change in capacitance in the parallel plate capacitor corresponding to stretching of the compliant portions in an axial direction confined to the plane of the parallel capacitive plates due at least in part to an expansion or contraction of the anatomical structure; and
   converting the sensed change in capacitance to a signal indicative of the respiratory function, using a processing element in communication with the strain-sensing device.

* * * * *